(12) United States Patent
Schauer et al.

(10) Patent No.: US 9,163,338 B2
(45) Date of Patent: Oct. 20, 2015

(54) FIBROUS MATS CONTAINING CHITOSAN NANOFIBERS

(75) Inventors: Caroline L. Schauer, Hulmeville, PA (US); Jessica D. Schiffman, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 1264 days.

(21) Appl. No.: 12/598,112

(22) PCT Filed: Apr. 11, 2008

(86) PCT No.: PCT/US2008/060013
§ 371 (c)(1),
(2), (4) Date: Apr. 15, 2010

(87) PCT Pub. No.: WO2009/011944
PCT Pub. Date: Jan. 22, 2009

(65) Prior Publication Data
US 2010/0216211 A1     Aug. 26, 2010

Related U.S. Application Data

(60) Provisional application No. 60/911,130, filed on Apr. 11, 2007.

(51) Int. Cl.
| | | |
|---|---|---|
| *A61K 8/73* | (2006.01) | |
| *A61K 8/02* | (2006.01) | |
| *D01F 9/00* | (2006.01) | |
| *A61L 27/20* | (2006.01) | |
| *D01D 5/00* | (2006.01) | |
| *D01F 1/10* | (2006.01) | |
| *D01F 11/00* | (2006.01) | |
| *D06M 13/123* | (2006.01) | |
| *D06M 101/02* | (2006.01) | |

(52) U.S. Cl.
CPC . *D01F 9/00* (2013.01); *A61K 8/027* (2013.01); *A61K 8/736* (2013.01); *A61L 27/20* (2013.01); *D01D 5/0038* (2013.01); *D01F 1/10* (2013.01); *D01F 11/00* (2013.01); *D06M 13/123* (2013.01); *A61L 2400/12* (2013.01); *B01D 2239/025* (2013.01); *B01D 2239/0407* (2013.01); *D06M 2101/02* (2013.01); *Y10T 428/249921* (2015.04)

(58) Field of Classification Search
CPC .............................. A61K 8/736; A61K 8/027
USPC ........................................................ 424/400
See application file for complete search history.

(56) References Cited

U.S. PATENT DOCUMENTS

2005/0095695 A1 * 5/2005 Shindler et al. ............. 435/285.1

FOREIGN PATENT DOCUMENTS

| KR | 10-0323253 B1 | 2/2002 |
|---|---|---|
| KR | 10-0545404 B1 | 1/2006 |
| KR | 10-0562013 B1 | 3/2006 |
| KR | 10-0652496 B1 | 12/2006 |

OTHER PUBLICATIONS

PCT Application No. PCT/US2008/060013 : International Search Report and Written Opinion of the International Searching Authority, Jul. 23, 2009, 13 pages.
Bhattarai et al, "Electrospun Chitosan-Based Nanofibers and Their Cellular Compatibility", Biomaterials, 2005, 26, 6176-6184.
Frenot, A. And Chronakis, I.S., "Polymer Nanofibers Assembled by Electrospinning", Current Opinion in Colloid and Interface Science, 2003, 8, 64-75.
Huang et al, "A Review on Polymer Nanofibers by Electrospinning and Their Applications in Nanocomposites", Composites Science and Technology, 2003, 63 2223-2253.
Ignatova et al, "Electrospun Nano-Fibre Mats With Antibacterial Properties From Quaternised Chitosan and Poly(Vinyl Alcohol)", Carbohydrate Research, 2006, 341, 2098-2107.
Kim et al, "Electrospinning Biomedical Nanocomposite Fibers of Hydroxyapaite/Poly(Lactic Acid) for Bone Regeneration", Journal of Biomedical Materials Research, Jul. 6, 2006, Part A, 643-649.
Li, I and Hsieh, Y, "Chitosan Bicomponent Nanofibers and Nanoporous Fibers", Carbohydrate Research, 2006, 341, 374-381.
Lu et al, "Electrospinning of Sodium Alginate With Poly(Ethylene Oxide)", Polymer, 2006, 47, 8026-8031.
Luoh, R. and Hahn, T., "Electrospun Nanocomposite Fiber Mats As Gas Sensors", Composites Science and Technology, 2006, 66 2436-2441.
Neamnark et al, "Electrospinning of Hexanoyl Chitosan" Carbohydrate Polymers, May 2006, 66, 298-305.
Ohkawa et al, "Electrospinning of Chitosan", Macromol. Rapid Commun. 2004, 25, 1600-1605.
Zhou et al, "Electrospinning of Chitosan/Poly(vinyl alcohol)/Acrylic Acid Aqueous Solutions", Journal of Applied Polymer Science, 2006, 102, 5692-5697.
PCT Application No. PCT/US2008/060013: International Search Report and Written Opinion of the International Searching Authority, Jul. 23, 2009, 13 pages.

* cited by examiner

*Primary Examiner* — Ruth Davis
(74) *Attorney, Agent, or Firm* — Baker & Hostetler LLP

(57) ABSTRACT

The invention relate to fibrous mats comprising chitosan nanofibers and, optionally, at least one filler material, at least one additive, or both. The invention also relates to methods of making same, and devices that include a fibrous mat comprising chitosan nanofibers.

22 Claims, 9 Drawing Sheets

Chitosan (A)

Glutaraldehyde (B)

FIBROUS MATS CONTAINING CHITOSAN NANOFIBERS

CROSS-REFERENCE TO RELATED APPLICATIONS

This application is the National Stage of International Application No. PCT/US2008/060013, filed Apr. 11, 2008, which claims the benefit of U.S. Provisional Application No. 60/911,130, filed Apr. 11, 2007, the disclosures of which are incorporated herein by reference in their entirety.

FIELD OF THE INVENTION

The invention concerns fibrous mats comprising fibers made of chitosan and optionally a filler and/or additive material, methods of producing same, and devices that include fibrous chitosan mats.

BACKGROUND OF THE INVENTION

Electrospinning is an inexpensive method for creating continuous, randomly oriented, nanofibrous mats from a variety of synthetic and natural polymers. These characteristics, in conjunction with the beneficial intrinsic effects of increased surface area from its nanofibrous form, make electrospun polymers ideal for medical, packaging, agricultural, filtration, protective clothing, nanocomposites, and automotive applications (Huang, Z.-M.; Zhang, Y. Z.; Kotaki, M.; Ramakrishna, S.; *Composites Science and Technology* 2003, 63, (15), 2223-2253).

Chitosan, a derivative of chitin (the second most abundant, naturally occurring, organic material after cellulose) is environmentally friendly, non-toxic, biodegradable, and anti-bacterial. It has been demonstrated that chitosan can be electrospun into fibrous mats with the aid of an additional polymer in solution. The additional polymer is typically either polyethylene oxide (PEO) (see Duan, B.; Dong, C.; Yuan, X; Yao, K. *J. Biomater. Sci., Polym. Ed.* 2004, 15 (6), 797-811, Geng, X; Kwon, O.-H.; Jang, *J. Biomaterials* 2005, 26 (27), 5427-5432, Spasova, M.; Manolova, N.; Paneva, D.; Rashkov, I. *e-Polymers* 2004, 56, 1-12, Bhattarai, N.; Edmondson, D.; Veiseh, O.; Matsen, F. A.; Zhang, M. *Biomaterials* 2005, 26, 6176-6184) or poly(vinyl alcohol) (PVA) (see Min, B.-M.; Lee, S. W; Lim, J. N.; You, Y; Lee, T. S.; Kang, P. H.; Park, W. H. *Polymer* 2004, 45, 7137-7142). However, when formed from chitosan and PEO and/or PVA, the resulting fibrous mats tend to contain a high content of PEO/PVA fibers and the characteristics of the mats reflect the low proportion of chitosan, i.e., the mats do not possess some or all of the advantageous characteristics associated with chitosan.

There remains a need for fibrous mats having advantageous physical properties with utility in such processes as filtration of gas and/or liquid.

SUMMARY OF THE INVENTION

The present invention relates to fibrous mats comprising (i) chitosan nanofibers and optionally, (ii) at least one filler material, one or more additives, or both. The disclosed fibrous mats may be substantially free of fibers of polyethylene oxide, fibers of poly(vinyl alchohol), or both. The weight percentage of chitosan nanofibers in the present fibrous mats, exclusive of any filler materials and additives, may be greater than 40 wt %, greater than 50 wt %, greater than 55 wt %, greater than 60 wt %, greater than 65 wt %, greater than 70 wt %, greater than 75 wt %, greater than 80 wt %, greater than 85 wt %, greater than 90 wt %, greater than 95 wt %, greater than 98 wt %, or greater than 99 wt %. Suitable fillers include clay, diatomaceous earth, calcium carbonate, metakaolinite, limestone, or mixtures thereof. Suitable additives include dyes, polymers, particles, nanoparticles, proteins, enzymes, and organic molecules. Suitable dyes include nile red and phthalocynanine green. Suitable polymers include hyaluronic acid, alginate, chitin, carboxymethylated chitosan. Suitable proteins and enzymes include those that can absorb, capture, degrade, denature, or otherwise deactivate or neutralize molecules or organisms that are harmful to human beings, examples of which include acetylcholine esterase and organophosphatase. Suitable organic molecules include crosslinkers. One preferred cross-linker is glutaraldehyde.

Some fibrous mats consist of cross-linked chitosan. In one embodiment, the chitosan fibers are cross-linked post processing using glutaraldehyde vapor. In a second embodiment glutaraldehyde liquid is used during fiber production. The cross-linking can occur either during fiber production (i.e., during electrospinning) or after the chitosan is spun into fibers.

In some embodiments, the nanofibers are made essentially of chitosan.

In certain embodiments, the nanofibers have an average diameter of about 50 to about 150 nanometers and, in some embodiments, about 58 to about 108 nanometers.

Another aspect of the invention concerns methods for forming a fibrous mat comprising: providing a solution of chitosan; and electrospinning the solution to form a fibrous mat comprising fibers of chitosan. Preferably, the solution of chitosan does not include polyethylene oxide or poly(vinyl alcohol). The solution may further comprise at least one additive material, at least one filler material, or both, the additive material, filler material, or both being optionally dissolved or suspended in the solution.

In some embodiments, the chitosan solution comprises a solvent comprising a tri-halo carboxylic acid. The solvent may be trifluoroacetic acid. In certain embodiments, the solution comprises a cross-linking agent. Following electrospinning, the spun chitosan may be cross-linked. Alternatively, the cross-linking may be performed during electrospinning. The cross-linking may be performed in the presence of glutaraldehyde. Additives may be added prior to electrospinning or following electrospinning, and additives may comprise dyes, polymers, organic molecules, particles, nanoparticles, or any combination thereof.

Also disclosed are devices comprising a chitosan mat in accordance with the present invention. Various filtration devices with residential, commercial, medical, industrial, and/or military utility may include any embodiment of the chitosan nanofiber mats described herein. In addition, various scaffold devices with medical, industrial, and/or military utility may include any embodiment of the chitosan nanofiber mats described herein.

DETAILED DESCRIPTION OF ILLUSTRATIVE EMBODIMENTS

Figure 1:
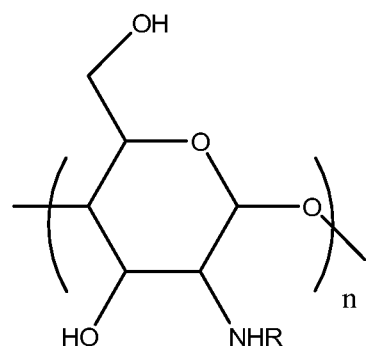
FIG. 1 shows the structures of chitosan (A) and glutaraldehyde (B) (GA).
Figure 1:
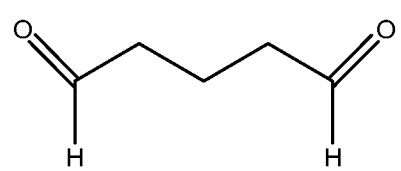

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "a filler" is a reference to one or more of such fillers and equivalents thereof known to those skilled in the art, and so forth. When values are expressed as approximations, by use of the antecedent "about," it will be understood that the particular value forms another embodiment. As used herein, "about X" (where X is a numerical value) refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable.

The disclosures of each patent, patent application, and publication cited or described in this document are hereby incorporated herein by reference, in their entirety.

The invention relates to fibrous mats comprising chitosan fibers and optionally, at least one filler material, at least one additive, or both, as well as methods for producing such fibrous mats. In some embodiments, unlike previous mats comprising chitosan fibers, the instant fibrous mats are substantially free of fibers of polyethylene oxide, fibers of poly (vinyl alcohol), or both, the presence of which are known to affect the characteristics of the fibrous mat. As used herein, a fibrous mat that is described as "substantially free" of fibers of polyethylene oxide, fibers of poly(vinyl alcohol), or both contains a quantity of polyethylene oxide, fibers of poly(vinyl alcohol), or both that corresponds to that which results from electrospinning a solution of chitosan that contains less than about 1 percent by weight polyethylene oxide, poly(vinyl alcohol), or both (i.e., the combined weight percentage of any polyethylene oxide and any poly(vinyl alcohol) in the solution is no more than about 1). In other embodiments, a fibrous mat that is described as "substantially free" of fibers of polyethylene oxide, fibers of poly(vinyl alcohol), or both contains a quantity of polyethylene oxide, fibers of poly(vinyl alcohol), or both that corresponds to that which results from electrospinning a solution of chitosan that contains less than about 0.5 percent by weight, less than about 0.2 percent by weight, less than about 0.1 percent by weight, or about zero percent by weight polyethylene oxide, poly(vinyl alcohol), or both (i.e., the combined weight percentage of any polyethylene oxide and any poly(vinyl alcohol) in the solution is no more than about 0.5, 0.2, 0.1, or zero, respectively).

The chitosan fibers are preferably nanofibers, i.e., have at least one dimension in the nanoscale range. For example, the chitosan fibers may have an average diameter of about 50 to about 125 nanometers, and more preferably about 55 to about 110 nanometers. In some embodiments, the chitosan fibers have an average diameter of about 58 to about 108 nanometers. The weight percentage of chitosan nanofibers in the present fibrous mats, exclusive of any filler materials and additives, may be greater than 40 wt %, greater than 50 wt %, greater than 55 wt %, greater than 60 wt %, greater than 65 wt %, greater than 70 wt %, greater than 75 wt %, greater than 80 wt %, greater than 85 wt %, greater than 90 wt %, greater than 95 wt %, greater than 98 wt %, or greater than 99 wt %.

Any filler that provides advantageous properties and does not interfere with the electrospinning process can be used in the instant invention. Suitable fillers include clay, diatomaceous earth, calcium carbonate, metakaolinite, limestone, carbon black, and mixtures thereof.

Likewise, any additive that provides advantageous properties and does not interfere with the electrospinning process can be used in the instant invention. An additive in accordance with the present invention may comprise about 0.01 wt % or more of the solution that is electrospun in order to produce the instant fibrous mats. Suitable additives include dyes, polymers, organic molecules, proteins, enzymes, particles, and nanoparticles. Suitable dyes include nile red and phthalocyanine green. The polymers may be, for example, biopolymers or polyelectrolytes. Nonlimiting examples of suitable polymers include hyaluronic acid, alginate, chitin, carboxymethylated chitosan, or any combination thereof. In some embodiments, the polymer is other than polyethylene oxide (PEO) and poly(vinyl alcohol) (PVA). Proteins and enzymes may include those that can absorb, capture, degrade, denature, or otherwise deactivate or neutralize molecules or organisms that are harmful to human beings, examples of which include acetylcholine esterase and organophosphatase, which are know to be effective in neutralizing sarin, a highly toxic nerve agent. Other proteins and enzymes for such purposes in the contexts of household, commercial, industrial, and/or military use will be readily appreciated by those skilled in the art.

Suitable organic molecules include cross-linkers. One preferred cross-linker is glutaraldehyde. When added to chitosan, the cross-linker may be a liquid or a vapor. Cross-linking may be performed following electrospinning of the chitosan, or may be performed during the spinning process. Particles and nanoparticles are preferably metallic species, more preferably transition metals, and may include manganese, gold, silver, copper, platinum, palladium, or any combination thereof.

Chitosan, 1, is a biopolymer which consists of β(1→4)-linked 2-acetamido-2-deoxy-β-D-glucose (N-acetylglucosamine):

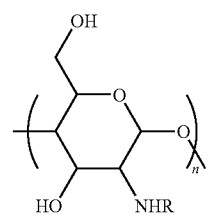

1 where R is H or C(=O)CH$_3$.

As a natural polymer, chitosan intrinsically exhibits enticing properties such as biocompatibility, biodegradability, and aqueous adsorption capabilities. These properties make chitosan an ideal polymer for a wide variety of fields and industrial applications including textiles (Dodane, V.; Vilivalam, V. D. *Pharm. Sci. Technol. Today* 1998, 1(6), 246-253), opthalmology (Kumar, M. N. V. R. *React. Funct. Polym.* 2000, 46 (1), 1-27), paper coatings (Vartiainen, J.; Motion, R.; Kulomen, H.; Ratto, M.; Skytta, E.; Ahvenainen, R. *J. Appl. Polym. Sci.* 2004, 94, 986-993), medical (Berger, J.; Reist, M.; Mayer, J. M.; Felt, O.; Peppas, N. A.; Gurny, R. *Eur. J. Pharm. Biopharm.* 2004, 57, 19-34), agricultural (Chirkov, S, N. *Appl. Biochem. Microbiol.* 2002, 38 (1), 1-8) and food (Shahidi, F.; Arachchi, J. K. V.; Jeon, Y.-J. *Trends Food Sci. Technol.* 1999, 10 (2), 37-51). However, processing chitosan can be challenging due to its tendency to coagulate with proteins at high pH, its insolubility in most solvent systems including water, and its high solution viscosity. Chitosan is known to be soluble in dilute organic acids (Hwang, J. K.; Shin, H. H. *Korea-Aust. Rheol. J.* 2000, 12 (3/4), 175-1791) such as acetic, formic, succinic, lactic, and malic acids. As disclosed herein, it has been surprisingly discovered that certain solvents, such as tri-halo carboxylic acids, including trifluoroacetic acid (TFA), may be used successfully to prepare chitosan solutions that can be subjected to electrospinning in order to form chitosan mats that are substantially free of PEO or PVA. For example, TFA may be used as a solvent, and the solvent may comprise aqueous TFA, e.g., about 50% to about 99% TFA combined with about 50% to about 1% H$_2$O, respectively. Table 1, below, depicts the results of tests conducted to determine the electrospinability of practical grade (PG) chitosan in TFA and trichloroscetic acid (TCA):

TABLE 1

| polymer | solvent(s) | % Acid | w/v (%) | solution observations | spinable? |
|---|---|---|---|---|---|
| PG chitosan | TFA | 100 | 2.667 | ideal viscosity, light yellow | yes |
| PG chitosan | TFA/H2O | 90 | 2.667 | looks ideal viscosity | no |
| PG chitosan | TFA/H2O | 85 | 2.667 | gel-like, some undissolved solid | no |
| PG chitosan | TFA/H2O | 80 | 2.667 | gel-like, some undissolved solid | no |
| PG chitosan | TFA/H2O | 75 | 2.700 | gel-like, some undissolved solid | no |
| PG chitosan | TFA/H2O | 50 | 2.700 | water-like viscosity, undissolved solids | no |
| PG chitosan | TCA | 100 | 2.667 | did not dissolve, yellow | no |

TABLE 1-continued

| polymer | solvent(s) | % Acid | w/v (%) | solution observations | spinable? |
|---|---|---|---|---|---|
| PG chitosan | TCA/H2O | 50 | 2.667 | did not dissolve, white | no |
| PG chitosan | TCA/H2O | 20 | 2.667 | did not dissolve, white | no |
| PG chitosan | TCA/H2O | 10 | 2.667 | did not dissolve, white | no |

Table 2, below, provides information relating to the characteristics of various forms of chitosan.

TABLE 2

Properties of Various Chitosans (As-Spun and Cross-linked After Production)

| | Low MW Chitosan | Medium MW Chitosan | High MW Chitosan | Practical-grade Chitosan |
|---|---|---|---|---|
| molecular weight (MW) | 70,000 | ~190,000-310,000 | 500,000-700,000 | 190,000->375,000 |
| percent deacetylation (%) | 74 | 83 | 72 | 75 |
| viscosity (cP) | 168 | 1116 | 308 | 308 |
| average as-spun fiber diameter (nm) | 74 ± 28 | 77 ± 29 | 108 ± 42 | 58 ± 20 |
| average cross-linked fiber diameter (nm) | 387 ± 183 | 172 ± 75 | 137 ± 59 | 261 ± 160 |
| Diameter increase due to cross-linking (%) | 423 | 123 | 26.9 | 350 |

The amine of chitosan can be used to cross-link the polymer by use of a variety of cross-linkers, including diisocyanates, Resimene (Ligler, F. S.; Lingerfelt, B. M.; Price, R. P.; Schoen, P. E. *Langmuir* 2001, 17 (16), 5082-5084), N,N-disuccinimidyl suberate (Schauer, C. L.; Chen, M.-S.; Chatterley, M.; Eisemann, K.; Welsh, E. R.; Price, R. R.; Schoen, P. E.; Ligler, F. S. *Thin Solid Films* 2003, 434 (1-2), 250-257), epichlorohydrin (Wei, Y. C.; Hudson, S. M.; Mayer, J. M.; Kaplan, D. L. *J. Polym Sci., Part A: Polym. Chem.* 1992, 30 (10), 2187-2193), gepinin (Jin, J.; Song, M.; Hourston, D. J. *Biomacromolecules* 2004, 5 (1), 162-168), and hexamethylene 1,6-di(aminocarboxysulfonate) (Welsh, E. R.; Schauer, C. L.; Qadri, S. B.; Price, R. R. *Biomacromolecules* 2002, 3 (6), 1370-1374). Glutaraldehyde (GA) has also been demonstrated to cross-link chitosan (Jameela, S. R.; Jayakrishnan, A. *Biomaterials* 1995, 16 (10), 769-775) through a number of proposed mechanisms. The first is by Michael-type adducts with terminal aldehydes, which lead to the formation of carbonyl groups (Scheme 1, right (Tual, C.; Espuche, E.; Escoubes, M.; Domard, A. *J. Polym. Sci., Part B: Polym. Phys.* 2000, 38 (11), 1521-1529)). The second main cross-linking method, Schiff base formation, leads to imine-type functionality (Scheme 1, left (Koyama, Y.; Taniguchi, A. *J. Appl. Polym. Sci.* 1986, 31 (6), 1951-1954)). In some embodiments, we utilize GA vapor to cross-link chitosan fibers and have observed Schiff base formation. In other embodiments, we utilize GA liquid to cross-link.

Scheme 1. Glutaraldehyde Cross-Links Chitosan either by a Schiff Base Imine Functionality (left) and/or by Michael-type Adducts with Terminal Aldehydes (right).

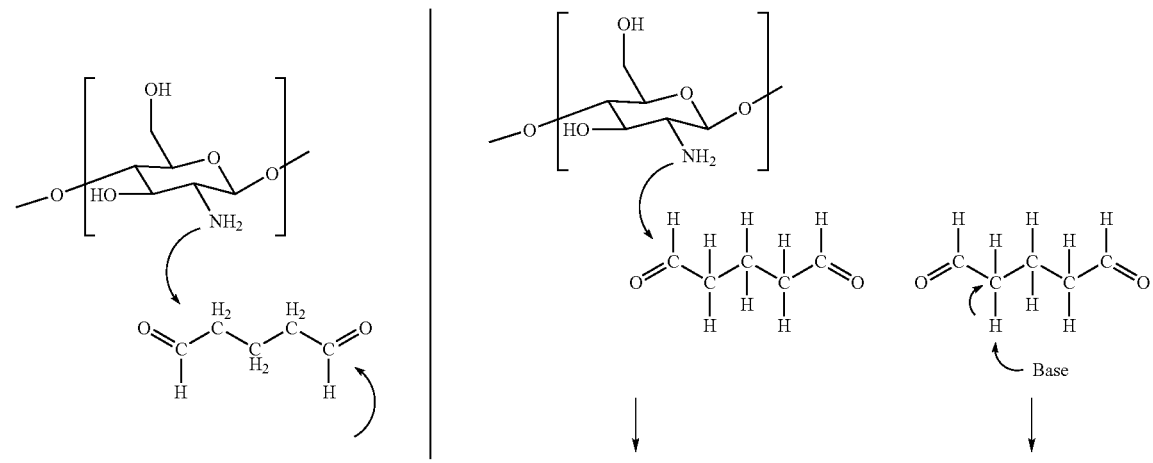

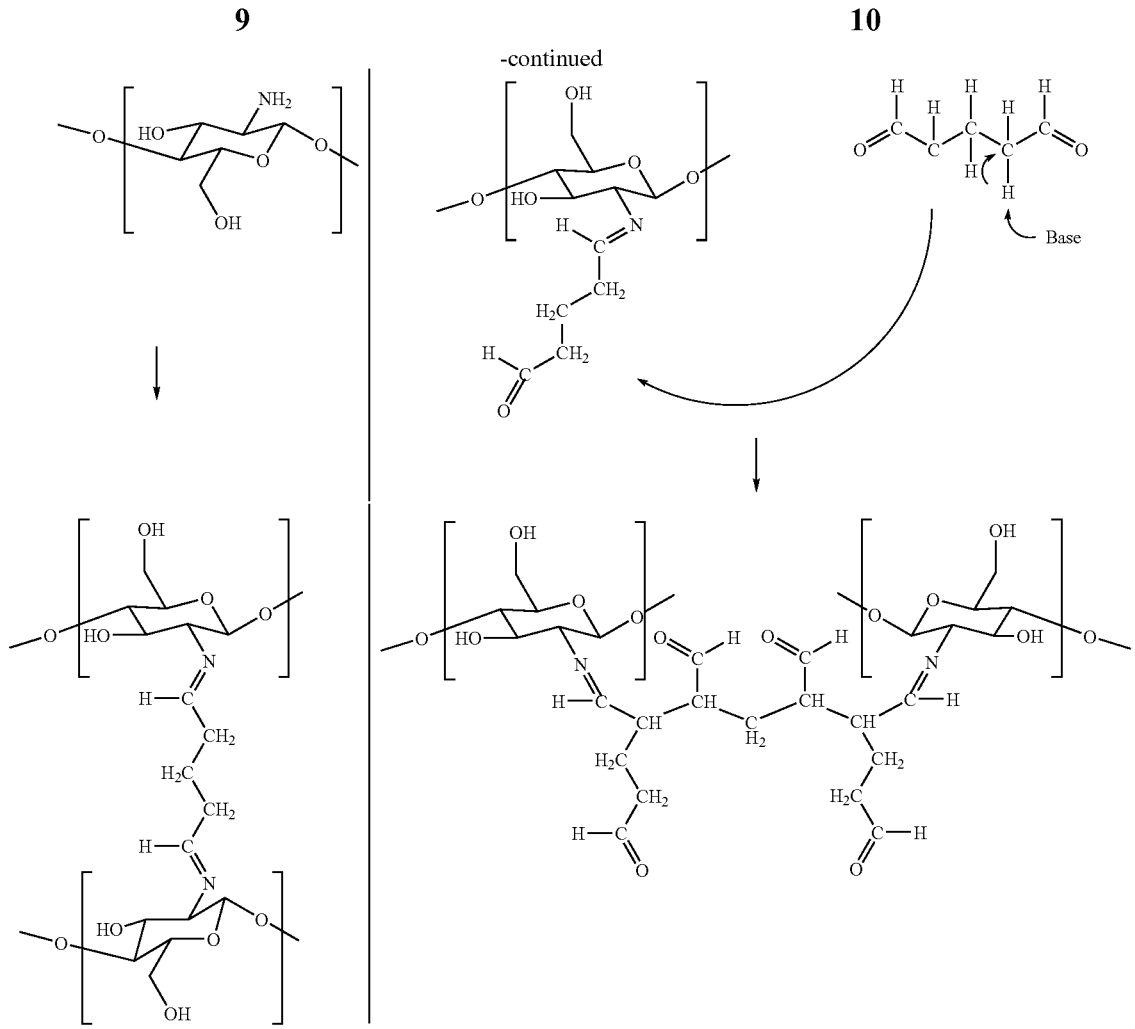

-continued

Electrospinning creates nonwoven fiber mats, with larger specific surface areas and smaller pores than conventional methods of fiber production, by utilizing electrostatic forces to create fibers; conventional methods such as melt spinning, dry spinning, and wet spinning rely on mechanical forces to produce fibers (Rutledge, G. C.; Shin, M. Y.; Warner, S. B.; Buer, A.; Grimler, M.; Ugbolue, S. C. *A Fundamental Investigation of the Formation and Properties of Electrospun Fibers*; University of Massachusetts Dartmouth and Massachusetts Institute of Technology: Cambridge, Mass., 1999; pp 1-10). In the electrospinning process, a polymer solution is advanced through a syringe with a needle on the end to form a Taylor cone (a conically shaped volume of fluid). A voltage drop is created between the needle and collector. When the electrostatic force is able to overcome the surface tension force and a thin jet will form and thin out over the course of three stages: jet initiation and extension in a straight line, whipping instability, and jet solidification and fiber collection (Kim, J. S.; Lee, D. S. J. Polym. Sci. 2000, 32 (7), 616-618).

The elements of an electrospinning apparatus include a high voltage supply, collector (ground) electrode, source electrode, and a solution or melt to be spun. The polymer solution can be held in place by a glass syringe with a metallic needle. Fibers form through the utilization of chain entanglement in the polymer solution. Fiber collection occurs on a suitable target. Such targets include a flat plate, wire mesh, wax paper, rotating drum, a human hand, etc.

Figure 7:
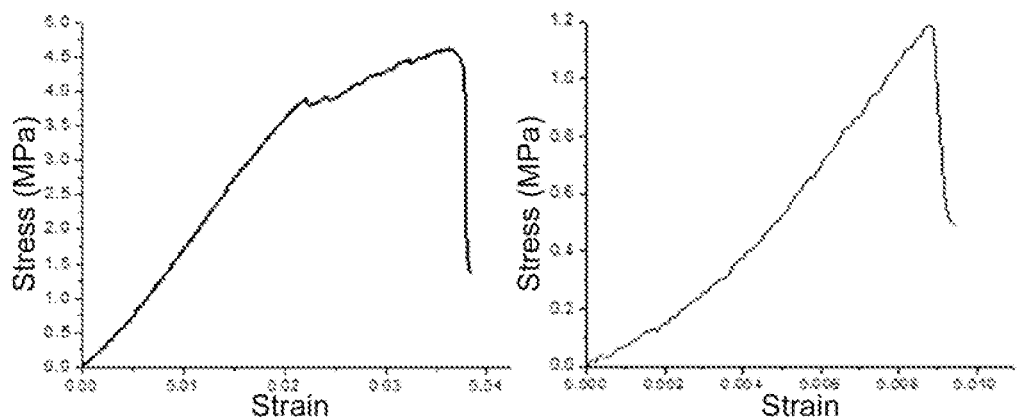
FIG. 7 shows stress-strain curve of electrospun medium MW chitosan mat (left) and vapor-cross-linked electrospun medium MW mat (right).

The as-spun medium molecular weight chitosan nanofibers have a Young's modulus of 154.9±40.0 MPa and are highly soluble in acidic and aqueous solutions. After crosslinking with GA vapor (FIG. 4), the medium molecular weight fibers increase in diameter, have a Young's modulus of 150.8±43.6 MPa, and are insoluble in basic, acidic, and aqueous solutions. FIG. 7 displays a typical stress-strain plot for both the as-spun (FIG. 2) and vapor-cross-linked (FIG. 4) electrospun chitosan fibers. The average Young's modulus of the chitosan mats were determined from the slope of the linear elastic region of the stress-strain curve and averaged amongst the samples. A pseudo-yield point is present in the as-spun fibers' stress-strain plot as evident by the second portion of the increasing slope that increases at a reduced rate. Hence, a reduced increase in modulus is observed, which corresponds to fiber alignment along the tensile pull axis. As the once randomly aligned fibers are being aligned, there is an increase in the allowable stresses until the break strain and ultimate tensile strength are achieved; they average 0.12±0.03 and 4.07±0.80 MPa respectively. The graph of the vapor-cross-linked medium MW fibers does not display the same pseudo yield point, but features a distinct maximum where the break occurred during tensile pulling. The vapor-cross-linked medium MW fibers have a lower average break strain of 0.10±(8.49×10-05) and additionally a decreased ultimate tensile strength of 1.19±0.0041 MPa than the as-spun fibers.

In some embodiments, a filler material is spun with the chitosan fibers. The filler can be dissolved in the spinning solution, or, alternatively, be suspended therein. Additives may also or alternatively be spun with the chitosan fibers, may be added after the electrospinning process, or may not be included at all. When included in an embodiment of the present invention, an additive can be added while in solution, in the form of a suspension, or attached post processing.

Figure 11:
FIG. 11 shows SEM images of as-spun electrospun chitosan/diatomaceous earth fibers (DE) (12% DE by weight). The displayed markers from left to right are 1 µm, 2 µm and 1 µm, respectively. Images were taken on the FESEM.
Figure 12:
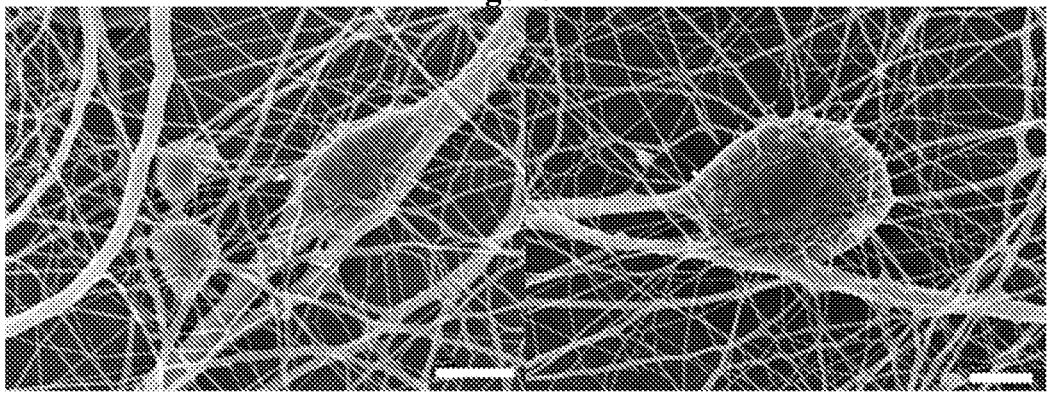
FIG. 12 shows SEM images of electrospun chitosan-calcium carbonate ($CaCO_3$) fibers (12% $CaCO_3$ by weight). Both figures have 4 µm markers displayed. Images were taken on the FESEM.
Figure 13:
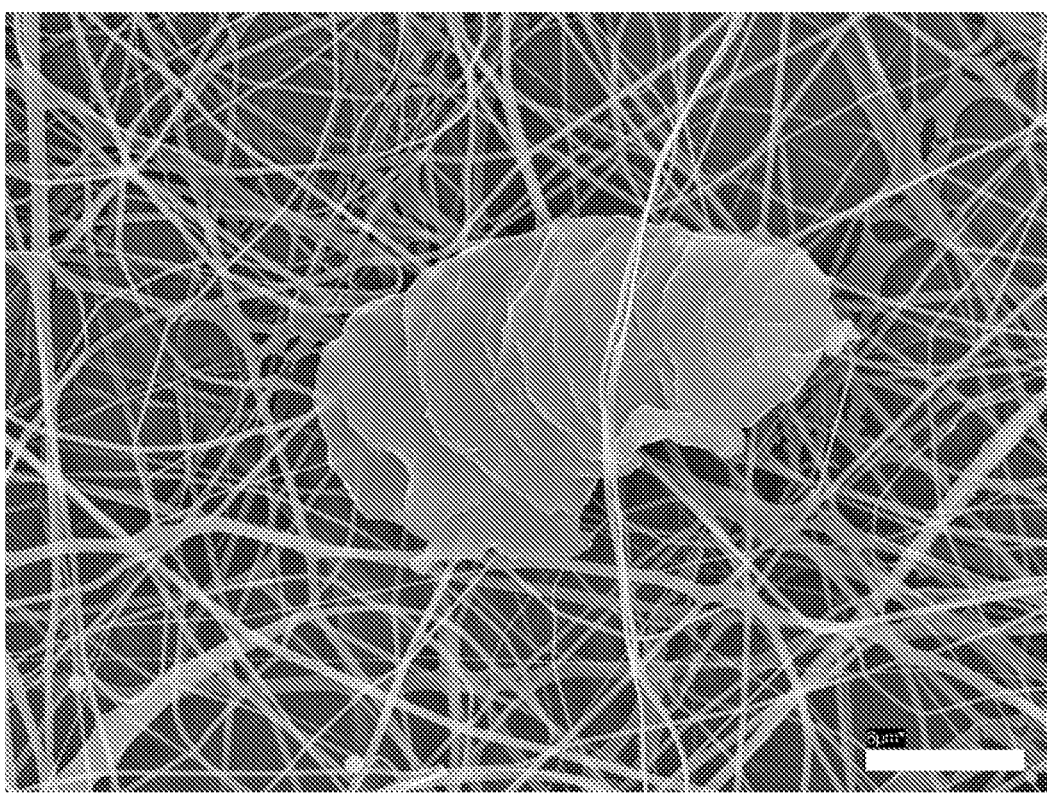
FIG. 13 shows an SEM image of chitosan-limestone (L) electrospun nanofibers (12% L by weight). A 6 µm marker is displayed. Image was taken on the FESEM.
Figure 14:
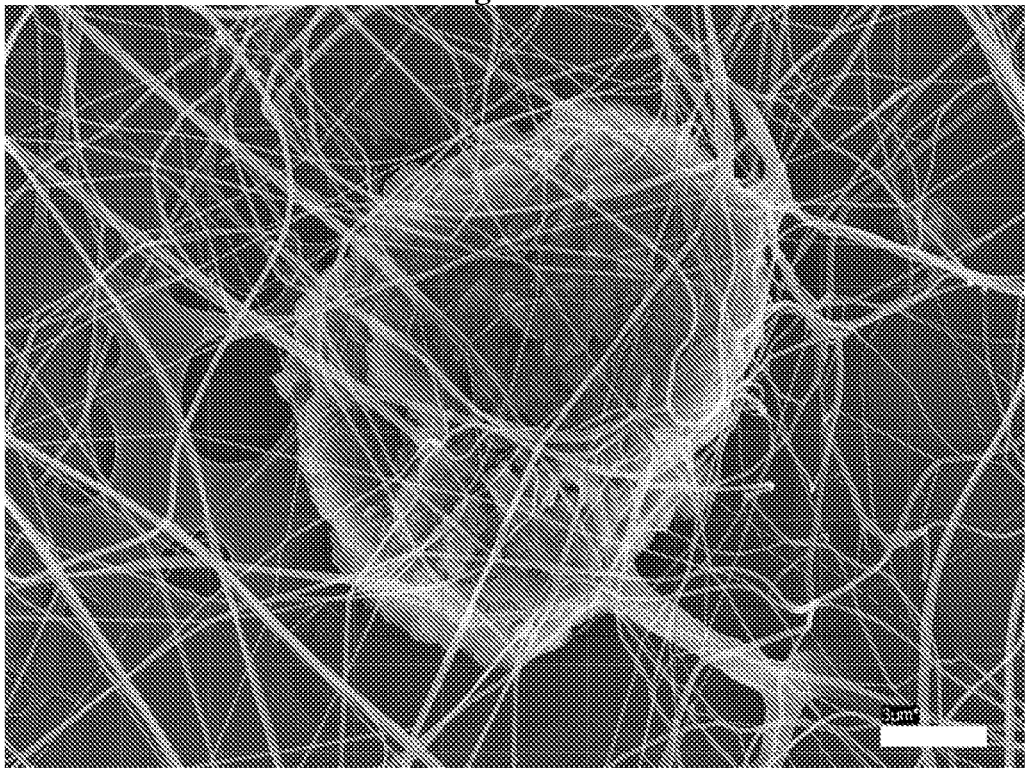
FIG. 14 presents an SEM image of chitosan-metakaolinite ($Al_2O_3 \cdot 2SiO_2$) electrospun fibers (12% $Al_2O_3 \cdot 2SiO_2$ by weight). A 4 µm marker is displayed. Image was taken on the FESEM.
Figure 15:
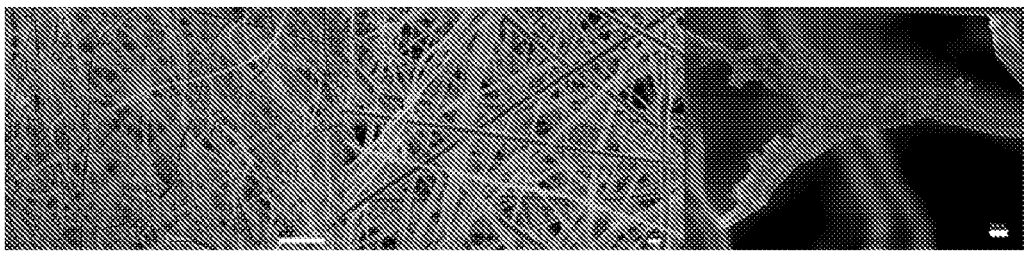
FIG. 15 presents SEM images of cross-linked chitosan-carbon black (CB) electrospun nanofibers. Images were taken on the FESEM. Left image is of vapor-cross-linked chitosan-CB fibers (25% CB by weight) with 10 µm marker, the middle image is of vapor-cross-linked chitosan-CB fibers (2.5% CB by weight) with 1 µm marker, and the right image is of vapor-cross-linked chitosan-CB fibers (25% CB by weight) with a 300 nm marker. Images were taken on the FESEM.
Figure 16:
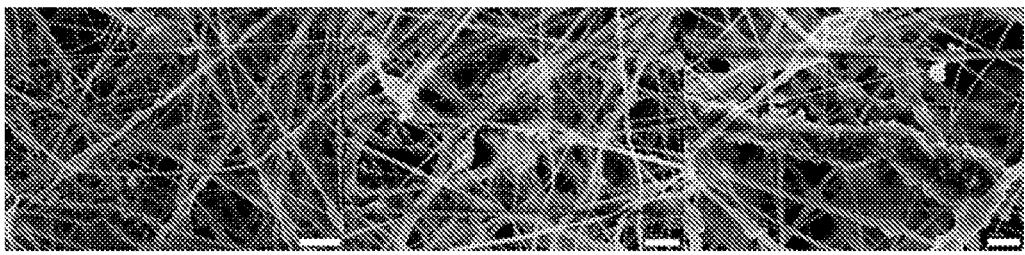
FIG. 16 presents SEM images of chitosan-carbon black (CB) electrospun fibers. From left to right the markers are 2 µm, 1.5 µm, and 750 nm respectively (All are 62.5% CB by weight). Images were taken on the FESEM.

One method that may improve the mechanical stability of the fibers is to add clay fillers. It was investigated whether electrospinning of chitosan was altered by the addition of a non-polymeric material, such as diatomaceous earth (DE). DE consists of fossilized remains of species of siliceous marine and fresh water unicellular organisms such as diatoms and other algae (Korunic, Z., *Diatomaceous Earths, a Group of Natural Insecticides*. J. of Stored Products Research, 1998. 34(2-3): p. 87-97). DE can be used for a variety of applications including: packing steam pipes, as a polishing abrasive, absorbent material, sealing wax, for preparing pigments, among other uses (Emmons, W. H., *General Economic Geology*. 1 ed. 1922, New York: McGraw-Hill Book Company, Inc. 517). As demonstrated in FIG. 11, DE can be electrospun with the chitosan fibers.

Also provided are devices comprising a chitosan mat in accordance with the present invention. Various filtration devices with residential, commercial, medical, industrial, and/or military utility may include any embodiment of the chitosan nanofiber mats described herein. In addition, various scaffold devices with medical, industrial, and/or military utility may include any embodiment of the chitosan nanofiber mats described herein. The present devices include an air filter, a liquid filter, or a scaffold comprising a fibrous mat comprising chitosan nanofibers and filler material, wherein the fibrous mat does not include fibers of polyethylene oxide or fibers of poly(vinyl alcohol). The filler material may comprise clay, diatomaceous earth, calcium carbonate, metakaolinite, limestone, carbon black, or mixtures thereof. In the present devices, the chitosan nanofiber mat may comprise about 0.1% to about 60% by weight of said filler material. The chitosan fibers may have an average diameter of about 50 to about 125 nanometers, and more preferably about 55 to about 110 nanometers. In some embodiments, the chitosan fibers have an average diameter of about 58 to about 108 nanometers. The fibrous mats of the inventive devices may include chitosan that has been cross-linked during fiber production, or after fiber production. The chitosan may be cross-linked using glutaraldehyde vapor.

The present devices also include an air filter, a liquid filter, or a scaffold comprising a fibrous mat comprising of chitosan nanofibers and at least one additive, wherein said fibrous mat does not include fibers of polyethylene oxide or fibers of poly(vinyl alcohol). Any additive that provides advantageous properties and does not interfere with an electrospinning process can be used in the instant devices. Suitable additives include dyes, polymers, organic molecules, biomolecules, proteins, enzymes, particles, and nanoparticles. Suitable dyes include nile red and phthalocyanine green. The polymers may be, for example, biopolymers or polyelectrolytes. Biopolymers and biomolecules may include those that support or promote bone or tissue ingrowth or otherwise compatibilize the present scaffolds with a biological situs. Nonlimiting examples of suitable polymers include hyaluronic acid, alginate, chitin, carboxymethylated chitosan, or any combination thereof. Proteins and enzymes may include those that can absorb, capture, degrade, denature, or otherwise deactivate or neutralize molecules or organisms that are harmful to human beings, examples of which include acetylcholine esterase and organophosphatase, which are know to be effective in neutralizing sarin, a highly toxic nerve agent. Other proteins and enzymes for such purposes in the contexts of household, industrial, and/or military use will be readily appreciated by those skilled in the art. Suitable organic molecules include cross-linkers. One preferred cross-linker is glutaraldehyde. When added to chitosan, the cross-linker may be a liquid or a vapor. Particles and nanoparticles are preferably metallic species, more preferably transition metals, and may include manganese, gold, silver, copper, platinum, palladium, or any combination thereof. For example, it is known that certain harmful industrial gases can be neutralized by contact with copper, and an air filter in accordance with the present invention may include copper particles in order to neutralize such gases. The present air filters, liquid filters, and scaffolds comprising a fibrous mat comprising of chitosan nanofibers and an additive may further comprising a filler material, wherein the filler material is clay, diatomaceous earth, calcium carbonate, metakaolinite, limestone, carbon black, or any combination thereof. The fibrous mat in the present filters or scaffolds may comprise about 0.1% to about 60% by weight of the filler material. The chitosan nanofibers may have an average diameter of about 50 to about 120 nanometers.

An air filter in accordance with the present invention may be a filter that is suitable for installation in, for example, a gas mask, or a active filtration device such as a movable piece of equipment for portable air remediation or in a fixed device for a residence, business, post office, hospital, military installation, or other structure frequented by humans or animals. The present air filters are effective for the remediation of air in buildings such as laboratories, manufacturing facilities, office buildings, medical facilities, or any places in which an accidental or deliberate (e.g., via terrorism) spill, leak, or other contamination of ambient air has occurred. Air filters made in accordance with the present invention can be effective in removing or neutralizing such airborne materials as heavy metals, acid fumes, spores, dust, mites, microorganisms, organic vapors, pesticides, asbestos, welding and soldering fumes, woodworking particles, various industrial gases, and other airborne toxins, particles, or contaminants. Those skilled in the art will readily appreciate the various situations and uses to which air filters in accordance with the present invention may be applied, each which are considered to fall within the scope of the present invention.

The liquid filters in accordance with the present invention may be used for the removal of a wide array of contaminants, toxins, particulate matter, microorganisms, and the like from various liquids, including water and other water-based liquids. The disclosed liquid filters may be used for the remediation or decontamination of water resources following the accidental or deliberate introduction of toxic chemicals, particles, or microorganisms, such as lead and other heavy metals, poisons, pesticides, spores, and other unwanted materials. Those skilled in the art will readily appreciate the various situations and uses to which liquid filters in accordance with the present invention may be applied, each which are considered to fall within the scope of the present invention.

Scaffolds in accordance with the present invention may function as structural matrices having medical, industrial, or military utility. For example, bone or tissue scaffolds may comprise the presently disclosed chitosan mats that optionally include one or more materials that permit, promote, or enhance biocompatibility, biological fixation, bone and/or tissue ingrowth, or other useful medical characteristics that render the bone or tissue scaffold safer, less likely to be rejected, more likely to provide structural support, more likely to be compatible with or encourage biological fixation, assimilation, and/or bone/tissue growth, among other beneficial characteristics. Many substances are incorporated into traditional bone and tissue implants, including collagen, gelatin, hydroxyapatite, etc., antiviricides, antimicrobials and/or antibiotics, amino acids, magainins, peptides, vitamins, inorganic elements, co-factors for protein synthesis, hormones, endocrine tissue or tissue fragments, synthesizers, enzymes such as collagenase, peptidases, oxidases, etc., polymer cell scaffolds with parenchymal cells, surface cell antigen eliminators, angiogenic drugs and polymeric carriers containing such drugs, biocompatible surface active agents, antigenic agents, cytoskeletal agents, cartilage fragments, living cells such as chondrocytes, bone marrow cells, mesenchymal stem cells, natural extracts, tissue transplants, bioadhesives, growth factors, growth hormones such as somatotropin, bone digestors, antitumor agents, fibronectin, cellular attractants and attachment agents, immunosuppressants, permeation enhancers, e.g., fatty acid esters such as laureate, myristate and stearate monoesters of polyethylene glycol, enamine derivatives, alpha-keto aldehydes, etc., nucleic acids; and, bioerodable polymers. These and other substances having medical utility may be included in the present scaffolds.

In other embodiments, structural scaffolds for use in manufacturing or industrial processes or final products may comprise the presently disclosed chitosan mats. There are many industrial applications in which light weight and/or high porosity are desired in a structural material; nonlimiting examples include for example, sporting equipment, such as skis, shin guards, helmets, and sneaker soles, watercraft components, airplane wings, insulation materials, shock and vibration absorbers, sound absorbers, and building materials. Scaffolds for such purposes and others may further include such materials as polyacrylates, polyepoxides, polyesters, polyurethanes, poly(methacrylic acid), poly(acrylic acid), polyimides, polysiloxanes, poly(glycolic acid), poly(lactic acid), polyamides, metals, glasses, ceramics, carbon, proteins, carbohydrates, nucleic acids, and lipids, which may enhance or otherwise functionalize the structural characteristics of the present scaffolds.

The invention is further illustrated by the following examples which are not intended as limiting.

Materials and Methods

All compounds were used as received. Low and high molecular weight (MW) chitosan were purchased from Fluka (Switzerland). Glutaraldehyde (GA), 97% pure sodium hydroxide (NaOH), 99.7+ ACS. reagent-grade acetic acid, ReagentPlus 99% trifluoroacetic acid (TFA), vile red and medium MW and practical-grade chitosan were purchased from Sigma-Aldrich (St. Louis, Mo.). Room-temperature ultrapure water (Millipore QPAK system) was used to make the solubility test solutions. One of the filler materials, metakaolinite, was from the Concrete Countertop Institute (Raleigh, N.C.). Calcium carbonate ($CaCO_3$) and carbon black, 100% compressed, were both from Alfa Aesar (Ward Hill, Mass.). Limestone was purchased from Old Castle Stone Products (Wyomissing, Pa.) and diatomaceous earth from Perma-Guard Inc. (Albuquerque, N.Mex.).

Solution Preparation

Chitosan/TFA solutions were prepared with low (70,000 Dalton), medium (~190,000 to 310,000 Dalton), or high molecular weight (MW) (500,000-700,000 Dalton) as well as practical grade (~190,000->375,000 Dalton) chitosan. In some solutions, a filler or additive material was added. Solutions were mixed for at least 24 h on an Arma-Rotator A-1 (Bethesda, Md.). When GA is added prior to electrospinning, the resultant fibrous mats are cross-linked since this is a method of reactive cross-linking Electrospinning The experimental electrospinning apparatus was set up as follows. After a 5 mL Luer-Lok Tip syringe (Becton Dickinson & Co, Franklin Lakes, N.J.) was repeatedly rinsed with TFA, 4 mL chitosan solution with or without additives was loaded into the syringe and a Precision Glide 21-gauge needle (Becton Dickinson & Co, Franklin Lakes, N.J.) was attached. By use of an alligator clip, the positive electrode of a high-voltage supply (Gamma High Voltage Research Inc., Ormond Beach, Fla.) was directly connected to the needle. The syringe was then placed on an advancement pump (Harvard Apparatus, Plymouth Meeting, Pa.), which was at a fixed distance of between 3 cm and 20 cm from the negative electrode that was clipped to a copper plate wrapped in aluminum foil. Between 10 kV and 30 kV was then applied between the positive and the negative anodes as the solution was advanced at a rate between 0.4 mL/h and 1.2 mL/h. Electrospinning parameters varied depending on what solution was being electrospun. The temperature (degrees Celsius) and percent humidity in the laboratory during electrospinning were monitored by a digital thermohygrometer (Fisher Scientific, Pittsburgh, Pa.).

Viscometry

The viscosities of the chitosan/TFA solutions that were successfully electrospun were determined on a Brookfield digital viscometer, model HTBD (Stoughton, Mass.), with the SC4-27 link hanging spindle rotating at 100 rpm. All viscosity experiments were conducted at room temperature (23° C.).

Cross-Linking

Chitosan fibers that were cross-linked after production were placed in a 11.43 cm×7.62 cm×5.08 cm vapor chamber (VWR Scientific Products, Bridgeport, N.J.) containing GA liquid. The GA liquid vaporized when it warmed to room temperature (23° C.). When fibrous mats are cross-linked using this method they are referred to as "vapor-cross-linked". An alternate method of cross-linking involved adding GA liquid to the chitosan/TFA solution prior to electrospinning When fibrous mats are cross-linked using this method they are referred to as cross-linked chitosan-GA.

Scanning Electron Microscope

Images of the chitosan fibers, cross-linked chitosan fibers, and fibers containing other additives were obtained with a Zeiss Supra 50/VP field emission scanning electron microscope (FESEM). The imaging of FIG. 3, as-spun chitosan fiber mats exhibiting branching, was conducted by use of a FEI/Phillips XL30 field emission environmental scanning electron microscope (FEESEM). Average fiber diameter of chitosan mats were obtained by use of the FESEM, by measuring 50 random fibers for each chitosan solution electrospun. Additional images after the mechanical testing was completed were taken of fibers close to their incident break face with the FESEM.

Solubility

Decreased solubility of the chitosan nanofibers due to cross-linking with GA was tested by subjecting as-spun and cross-linked chitosan mats to basic, acidic, and aqueous solutions. This testing also helped to identify if filler material was well incorporated into the fibers within the fibrous mats. Fifteen-$mm^2$ petri dishes (Becton Dickinson, Franklin Lakes, N.J.), each containing 30 mL of solution, were utilized. Basic solution was 1 M NaOH, acidic solution was 1 M acetic acid, and aqueous solution was ultrapure water. 2.54 cm×1.27 cm samples of as-spun or cross-linked chitosan fibrous mats, some of which contained an additive, were placed into each solution. After 15 min, if possible, one of the mats was removed, while the other remained in the solution for 72 h or longer. The solubility and integrity of the mats over the time elapsed was visually inspected.

Fourier Transform Infrared Spectroscopy

Attenuated reflectance using a Fourier transform (Excalibur FTS-3000) spectroscopy was taken. All spectra were taken in the spectral range of 4000-500 $cm^{-1}$ by accumulation of 64 scans and with a resolution of 4 $cm^{-1}$.

X-ray Diffraction

A D500 Siemens XRD with a CuKa source was utilized to obtain XRD patterns of one-step cross-linked chitosan/carbon black fibrous mats mounted onto glass slides wrapped with store purchased aluminum (Al) foil. Scans were taken 5-30° with hold time of 0.04 s. Peak detection and subtraction of Al foil peaks using the MDI JADE 7 software.

Experimental Results

Viscometry

Using the appropriate molecular weight polymer conjoined with idealizing the viscosity of the polymer solution is an imperative step toward electrospinning Normally, the higher of two molecular weight polymers dissolved in a solvent will result in higher viscosity. While the viscosity of the four chitosan/TFA solutions varied, they all were found to successfully yield fibers. The viscosity (Table 2) of the low and medium MW chitosan solutions was found to be 168 and 1116 cP, respectively. The high MW and the practical-grade chitosan were determined to have the same viscosity: 308 cP. All solutions tested were the same weight to volume ratio of chitosan to acid, which were created and tested in triplicate during the same testing session over which lab temperature and ambient humidity remained constant. We note that the percent deacetylation was found to be ~10% higher for the medium MW chitosan than for the others. The source of the chitin from which the chitosan has been derived from remains unknown for all bulk chitosan processed. We speculate that the variability observed was due to the intrinsic differences including the multitude of chain entanglement and conformations within the chitosan.

Scanning Electron Microscopy

Figure 2:
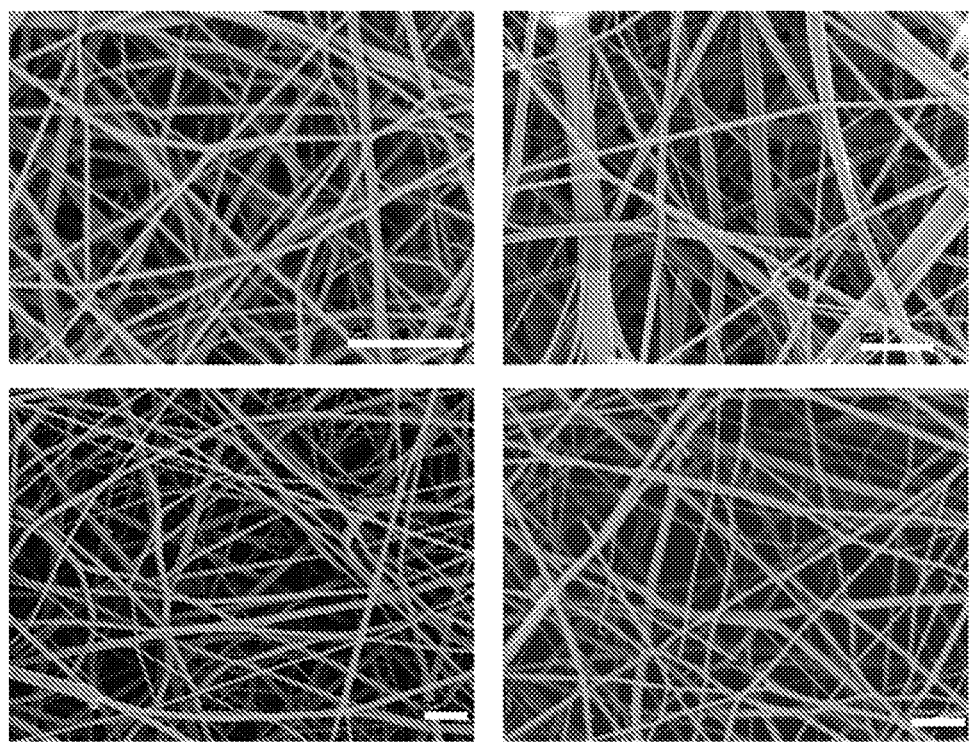
FIG. 2 presents SEM images of electrospun chitosan fibers from low molecular weight (MW) with 1 μm marker (top left), medium MW with 1 μm marker (top right), high MW with 1 μm marker (bottom left), and practical-grade with 500 nm marker (bottom right) chitosan. Images were taken on the FESEM.

All chitosan/TFA solutions produced fine, cylindrical, continuous, and randomly oriented fibers. FIG. 2 displays SEM micrographs of the various as-spun chitosan fibers including low MW (top left), medium MW (top right), high MW (bottom left), and practical-grade (bottom right). Average fiber diameter size was determined by averaging the diameter of 50 random fibers; the smallest and largest diameter measurement were included in this average. Average fiber diameter (Table 2) increased as the MW increased for the low, medium, and high MW chitosan and were found to be 74±28, 77±29, and 108±42 nm, respectively. The MW of practical-grade chitosan was comparable to that of the medium MW chitosan, and fibers electrospun from the practical-grade chitosan were within standard deviation from the medium MW fibers. Average diameter of the electrospun practical grade chitosan was of 58±20 nm. To define the range of diameters observed, the smallest and largest diameters measured for the various electrospun fibers are quoted. The smallest and largest fiber diameters measured were 37 and 170 nm for low MW, 31 and 174 nm for medium MW, 45 and 226 nm for high MW, and 28 and 120 nm for practical-grade chitosan. These diameter measurements also include the required sputter-coated layer of platinum (approximately 5-10 nm) that is applied prior to viewing the fiber diameters.

Figure 3:
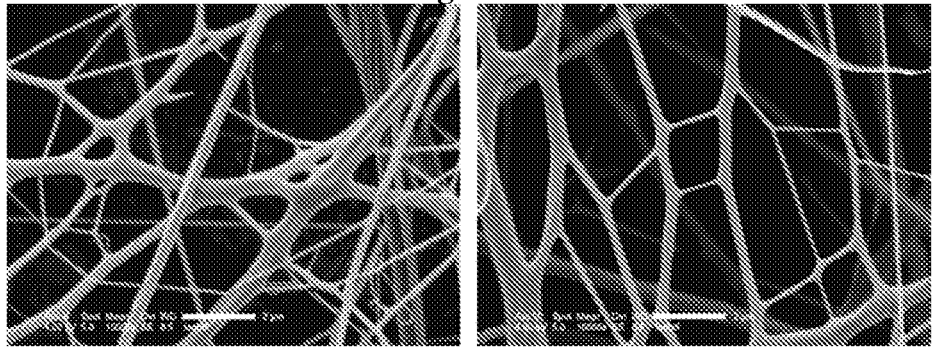
FIG. 3 presents SEM images displaying branched morphology of electrospun mats composed of low MW chitosan with 2 µm marker (left) and practical-grade chitosan with 2 µm marker (right). Images were taken on the FEESEM.

In our experiments, as observed in FIG. 3, branching sometimes occurred in the low MW (left image) and the practical-grade (right image) chitosan mats. (The split fiber that is apparent in the low MW SEM image is a result of beam burning; the original fiber was continuous.) In order for non-branched fibers to be electrospun, an appropriate level of competition between electrical forces and surface tension must be maintained. Alterations from this state can result from elongations of the jet or evaporation of solvent, which can cause jet splitting that consequently results in the branching of fibers. While not intending to be bound by theory, this phenomenon may be due to the presence of nonuniformly dispersed charges and molecular weight in the low molecular weight material. Our finding show that low MW fibers exhibited some branching, which was possibly due to the intrinsically low MW of the bulk chitosan. Practical grade chitosan resulted in branching, which might be attributed to the non-uniformity of the raw material; it is known that practical-grade chitosan may contain foreign matter. This nonuniformity leads to branching because as the polymer solution is advanced; the electrostatic repulsion forces overcome the surface tension at the tip of the needle in some locations (where foreign matter is located). As previously noted, the competition between these two forces is a delicate balance that must be maintained to guarantee the production of ideal fibers.

Again, while not wanting to be bound by theory, an alternative reason why this branching might have occurred is due to the environment in which the fibers were electrospun instead of the bulk chitosan qualities. While all chitosan fibers were created at approximately the same temperature (20-25° C.), there was a large discrepancy in the percent humidity that was measured. The fibers that exhibit branching (FIG. 3) were created in the 20-25% humidity range while the fibers that did not exhibit this morphology (FIG. 2) were spun when the humidity was twice as high, 40-45% humidity. It is possible that branching did not occur when the humidity level was elevated because solvent evaporation, due to the excess moisture levels in the air, occurred at a slower rate. Thus, in some embodiments, creating an atmosphere within the electrospinning apparatus that will hold both the temperature and humidity constant will be desirable.

Figure 4:
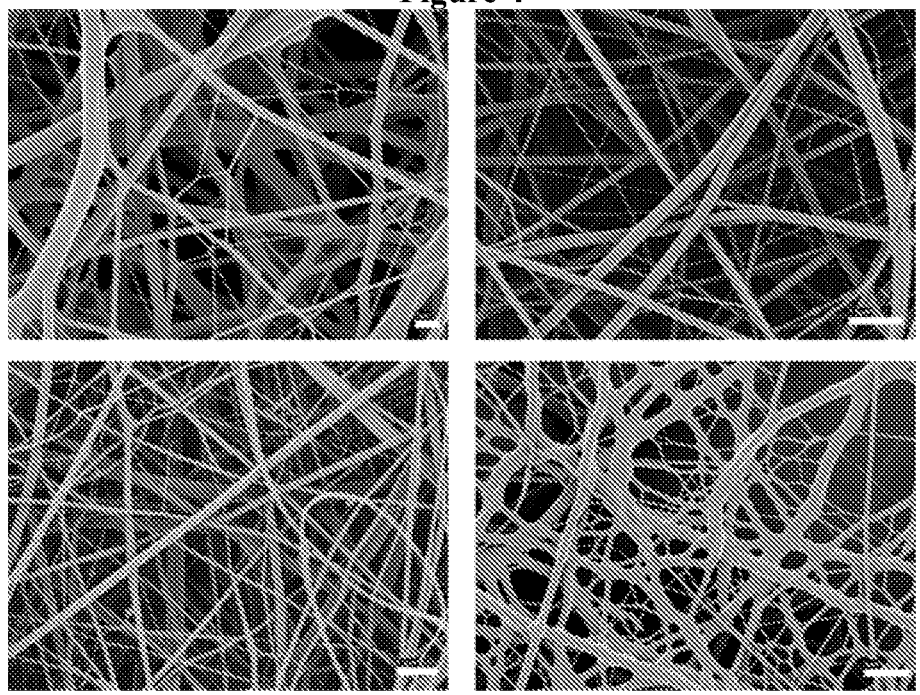
FIG. 4 presents SEM image of vapor-cross-linked electrospun chitosan fibers from low MW with 1 µm marker (top left), medium MW with 1 µm marker (top right), high MW with 1.3 µm marker (bottom left), and practical-grade with 3 µm marker (bottom right) chitosan. Images were taken on the FESEM.
Figure 17:
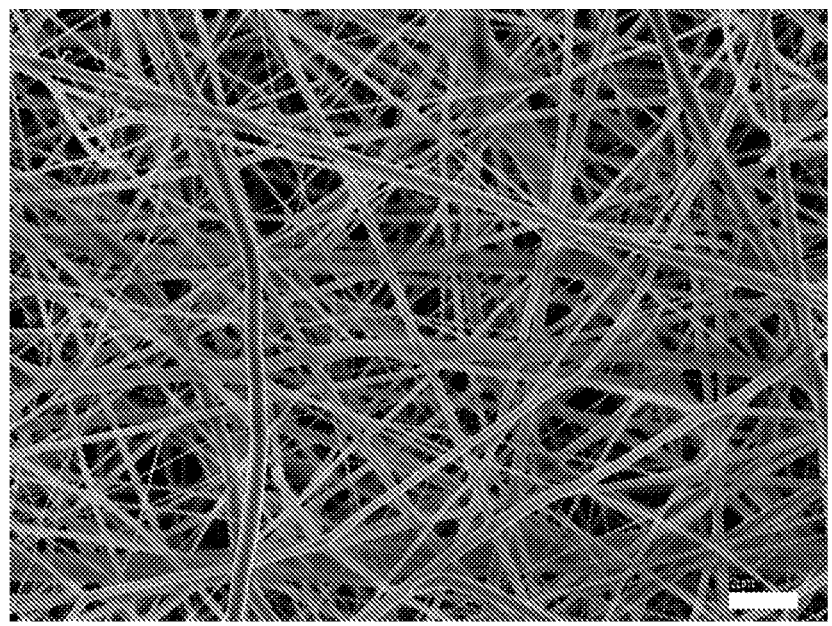
FIG. 17 presents an SEM image of electrospun chitosan-GA fibers (0.4 g/1 mL w/v of chitosan/GA). These fibers are cross-linked during the electrospinning process. A 2 µm marker is displayed. Image was taken on the FESEM.

To cross-link the as-spun chitosan fiber mats, they were placed in a vapor chamber with GA vapor. FIG. 4 displays SEM images of vapor-cross-linked electrospun chitosan fibers from low (top left), medium (top right), and high MW (bottom left), as well as practical-grade (bottom right) chitosan. From all of the SEM images, it is evident that after cross-linking the fiber mats retain their integrity as long, randomly oriented, cylindrical fibers. FIG. 17 displays a micrograph of chitosan fibers that were cross-linked during production. This image displays that the chitosan fibers that are cross-linked during their production are additionally long, randomly oriented, and cylindrical.

Figure 5:
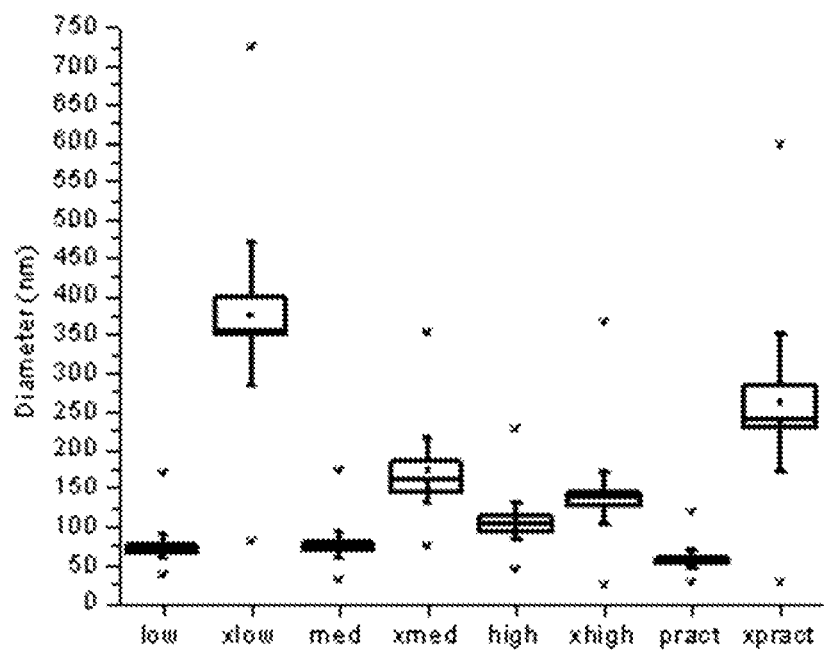
FIG. 5 shows box plots displaying the diameter size distribution of fiber diameters for the various electrospun chitosans: from left to right, low MW, vapor-cross-linked low MW, medium MW, vapor-cross-linked medium MW, high MW, vapor-cross-linked high MW, practical-grade, and vapor-cross-linked practical-grade. The box outline is the standard error, the square inside the box is the mean data point, the line inside the box is the median data location, and the whiskers display the upper (x) first/99th percentile.
Figure 18:
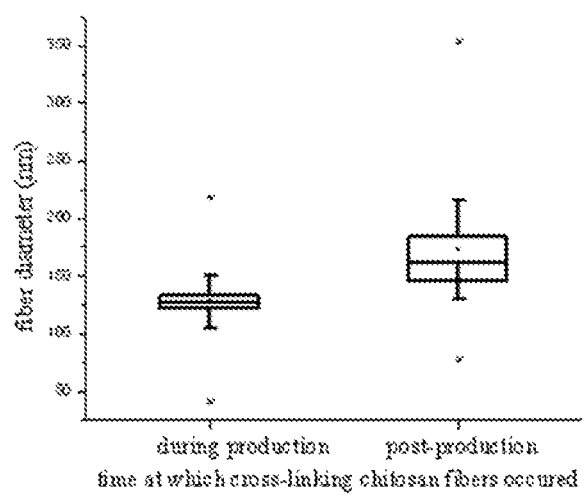
FIG. 18 shows box plots displaying the diameter size distribution of fiber diameters for chitosan fiber mats that were cross-linked during electrospinning (left) and post-electrospinning (right). The box outline is the standard error, the square inside the box is the mean data point, the line inside the box is the median data location, and the whiskers display the upper (x) first/99th percentile.
Figure 19:
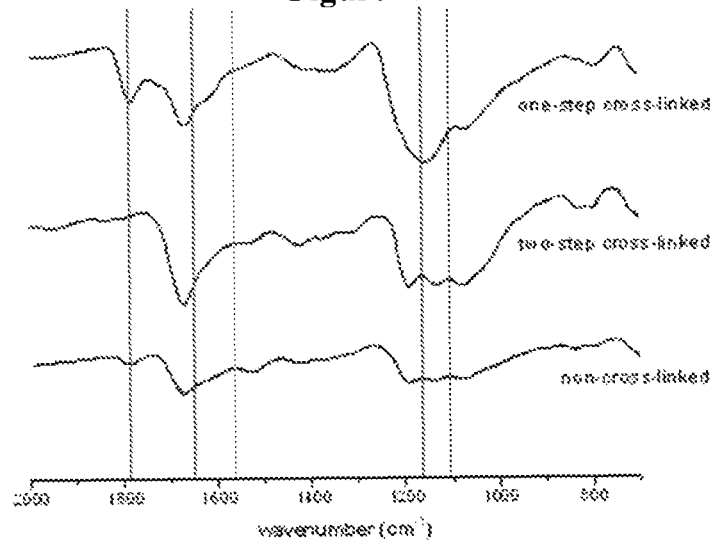
FIG. 19 presents FTIR spectra of as-spun medium MW fibrous mats (bottom), vapor cross-linked medium MW chitosan fibrous mat (middle), cross-linked medium MW chitosan-GA fibrous mat (top).

Average fiber diameters for the cross-linked chitosan fiber for the low, medium, and high MW and practical-grade chitosan were found to be 387±183, 172±75, 137±59, and 261±160 nm, respectively (Table 2). The smallest and largest fiber diameters measured were 80 and 725 nm for low MW, 76 and 353 nm for medium MW, 23 and 365 nm for high MW, and 26 and 596 nm for practical-grade chitosan. Generally, the smaller as-spun fibers experienced a higher increase in average diameter upon cross-linking This could possibly be a result of their higher ratio of surface area to volume. Additionally, as the GA cross-links the chitosan a spreading of the molecules occurs. FIG. 5 displays a box plot of the fiber size distributions for both the as-spun and cross-linked post-production electrospun chitosan fibers. The box outline is the standard error, the square inside the box is the mean data point, the line inside the box is the median data location, and the whiskers display the upper inner and lower inner fence values. Above and below the whiskers, "+" indicates the max/min data point and "x" indicates the first/99th percentile (these values appear to overlap in the figure). The upper inner fence whisker extends to the 75th percentile plus 1.5 times the interquartile range, while the lower inner fence value extends down to the 25th percentile minus 1.5 times the interquartile range. Data points that lie outside the fence values are considered outliers. Outliers and individual data points were not plotted on the provided graph. Since the as-spun fibers are next to their cross-linked counterparts, it is apparent that most of the data points for the vapor-cross-linked fibers are greater than the as-spun chitosan nanofibers. FIG. 18 is a box plot that compares the fiber size distribution of cross-linked chitosan fiber mats. From this figure, it is evident that fibers that were cross-linked during their production (left) on average have a smaller diameter than fibers that are cross-linked post-production (right).

Fourier Transform Infrared Spectroscopy.

Figure 8:
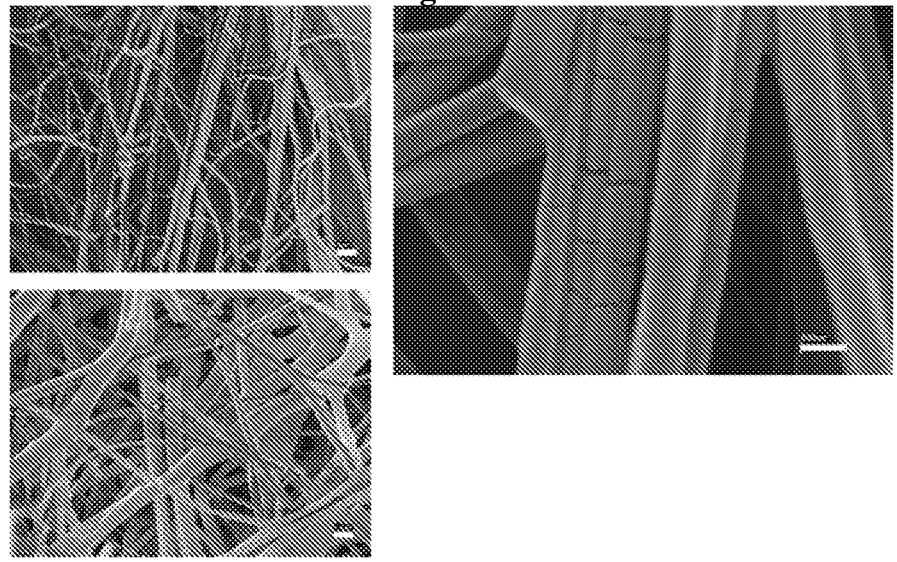
FIG. 8 presents SEM images of electrospun chitosan fibers after mechanical testing close to their breaking point: overall alignment of as-spun medium MW chitosan fibers with 3 µm marker (upper left); overall structure of vapor-cross-linked medium MW chitosan fibers with 1.3 µm marker (lower left); close-up of as-spun medium MW chitosan fibers with 500 nm marker (right). Images were taken on the FESEM.
Figure 9:
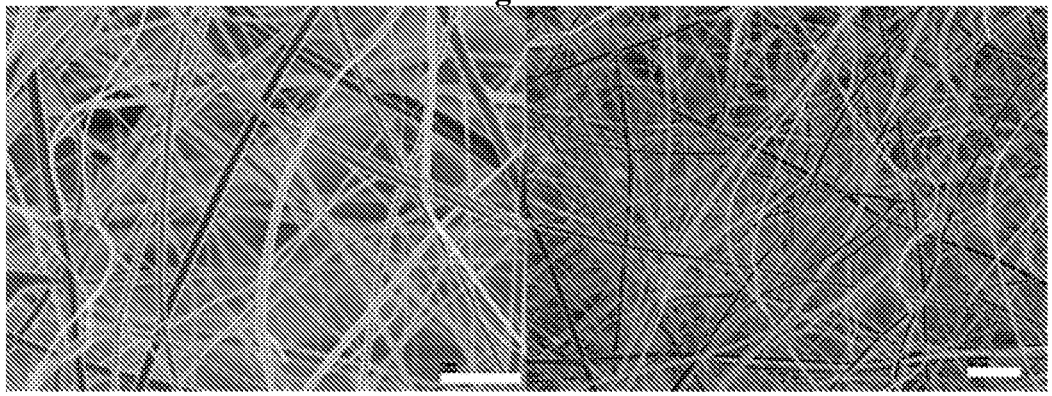
FIG. 9 shows SEM images of vapor-cross-linked chitosan-hyaluronic acid electrospun nanofibers (20% HA by weight). The images contain have a 2 µm marker (left) and a 10 µm marker (right). Images were taken on the FESEM.
Figure 10:
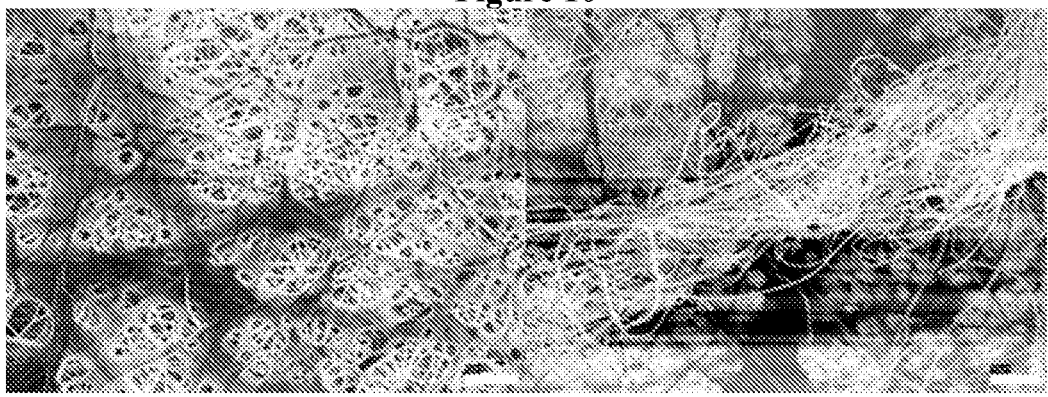
FIG. 10 presents SEM images of chitosan-nile red electrospun fibers. (0.15% nile red by weight.) There is a 5 µm marker displayed in the left image and a 10 µm marker displayed in the right image. Images were taken on the FESEM.

FTIR spectra are displayed in FIG. 8 of the bulk chitosan samples and of the electrospun mats before and after cross-linking with vapor-GA. By use of a combination of the OH stretching band at 3450 cm$^{-1}$, amide I bands at 1655 and 1630 cm$^{-1}$, amide II band at 1560 cm$^{-1}$, C—H stretching band at 2877 cm$^{-1}$, the bridge oxygen stretching band at 1160 cm$^{-1}$, and the C—O stretching bands at 1070 and 1030 cm$^{-1}$, the percent deacetylation can be determined. Current literature provides seven different peak ratios (1560/1070, 1560/1030, 1630/2878, 1655+1630/2878, 1550/2878, 1655/3450, and 1655/2867) that have been investigated to determine the percent deacetylation of chitosan. Additionally, Roberts and co-workers (Baxter, A.; Dillon, M.; Taylor, K. D. A.; Roberts, G. A. F. Int. J. Biol. Macromol. 1992, 14, 166-169) and Miya and co-workers (Miya, M.; Iwamoto, R.; Ohta, K. M. S. Kobunshi Ronbunshu 1985, 42 (3), 181-189) each utilized alternative methods of baseline correction used for peak height analysis. Generally, the greatest source of error, when calculating percent deacetylation via FTIR, is from bulk water, which can provide up to 1% error even in well-dried samples.

Using on the work of Shigemasa et al. (Shigemasa, Y.; Matsuura, H.; Sashiwa, H.; Saimoto, H. Int. J. Biol. Macromol. 1996, 18 (3), 237-242) as a foundation, the 1560/1070 peak ratio was used to determine the percent deacetylation of the bulk chitosan samples. On the basis of the FTIR spectra of the bulk chitosan materials, the low MW chitosan was 74%, the medium MW was 83%, the high MW was 72%, and the practical-grade was 75% deacetylated.

Chitosan fiber samples were evaluated by attenuated reflectance FTIR; the whole fibers were analyzed directly. Of importance for the spectra of the as-spun chitosan fibers was the presence of trifluoroacetic acid that was used to electrospin the chitosan; the peak at 1750 cm$^{-1}$ indicated the presence of a carboxylic acid.

As a result of the cross-linking reaction, significant changes are observed in the FTIR spectra of the as-spun versus cross-linked electrospun fibers. The FTIR spectra of cross-linked chitosan fibers displayed a distinct change in the carbonyl-amide region. The primary amine peak decreased when the chitosan fibers were cross-linked, while a new peak for C=N imine appeared. According to the literature, the C=N peak can be anywhere from 1620 to 1660 cm$^{-1}$. (Knaul, J. Z.; Hudson, S. M.; Creber, K. A. M. J. Polym. Sci., Part B: Polym. Phys. 1999, 37 (11), 1079-1094). This appeared as a strong split peak at 1650 cm$^{-1}$. The peak at 1560 cm$^{-1}$ (shown by asterisks in FIG. 6) disappeared in the cross-linked chitosan fibers due to the loss of the free amines, indicating that the fiber mats exhibited a Schiff base imine functionality just as Taul et al. (Tual, C.; Espuche, E.; Escoubes, M.; Domard, A. J. Polym. Sci., Part B: Polym. Phys. 2000, 38 (11), 1521-1529) reported in their chitosan/GA film experiment. Our experiments exhibited a color change—namely, our mats became yellow upon cross-linking (as-spun mats were white). Finally, to confirm that Michael-type cross-linking did not occur, we note that no identifiable carbonyl groups appear in the 1720-1730 cm$^{-1}$ IR spectra.

Solubility

As-spun chitosan fibers with and without additives as well as both kinds of cross-linked chitosan fibers with and without additives were immersed in acetic acid, water, and NaOH solutions. When the as-spun chitosan mats were subjected to acetic acid solution, they appeared to disintegrate instantaneously: the fibers dissolved and neither the mat nor individual fibers remained. The as-spun fibers dispersed instantly in the ultrapure water; there was no form retention. Upon looking very carefully in the water, cloudy white specks could be seen. Therefore, perhaps some agglomeration of nanofibers remained since an opaque white color was visible with the unaided eye. It is certain, however, that the mat instantly broke apart upon interacting with water and could not be recovered. When subjected to the NaOH solution, the as-spun chitosan fiber mats survived. They remained white and rectangular in shape for both the 15 min and the 72 h test.

All cross-linked chitosan fiber mats with and without additives or fillers behaved in a different manner from the as-spun mats; they survived the acetic acid, ultrapure water, and NaOH solutions for 15 min. Additionally, after 72 h the fiber mats looked the same; their rectangular shape and yellow color were retained. After the cross-linked chitosan fiber mats were removed from the solutions, visual inspection implies that their shape and rigidity remained unaltered.

Mechanical Testing

Figure 6:
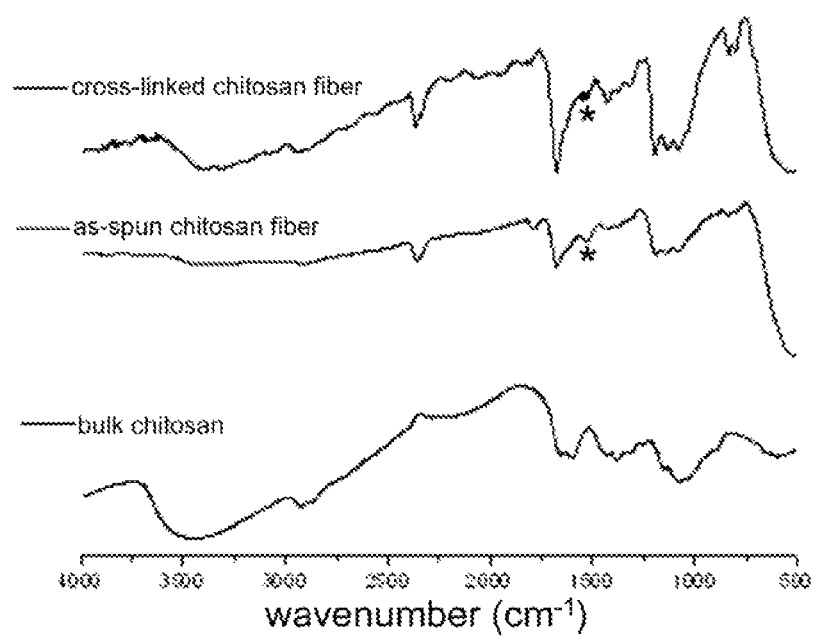
FIG. 6 presents FTIR spectra of vapor cross-linked electrospun medium MW chitosan fibrous mat (top), electrospun medium MW chitosan fibrous mat (middle), and bulk sample of medium MW chitosan (bottom).
Figure 20:
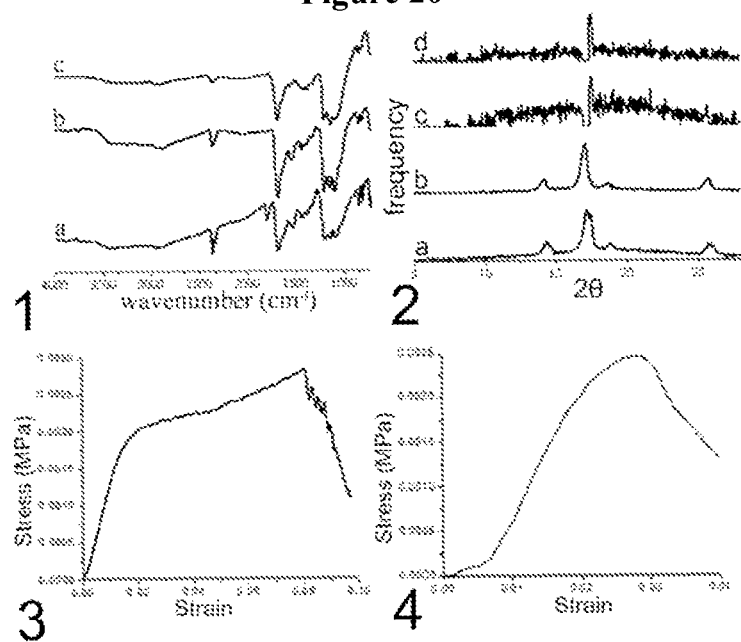
FIG. 20 displays (1) FTIR spectra of (a) as-spun medium MW chitosan, (b) as-spun medium MW chitosan/carbon black (2.5%), and (c) vapor-cross-linked medium MW chitosan/carbon black (2.50%) mats. (2) XRD patterns taken on cross-linked chitosan-GA fibrous mats containing (a) 0.00%, (b) 2.50%, (c) 6.25%, and (d) 50.0% carbon black. (3) Stress-strain curve of as-spun medium MW chitosan/carbon black (2.50%) mat, and (4) Stress-strain curve of vapor-cross-linked medium MW chitosan/carbon black (2.50%) mat.

The mechanical properties of both the as-spun and vapor-cross-linked randomly oriented chitosan fibrous mats with and without additives or fillers were determined on a Kawabata microtensile tester; the findings were supported by the subsequently provided SEM images. FIG. 6 displays a typical stress strain plot for both the as-spun (FIG. 6, left) and cross-linked (FIG. 6, right) electrospun medium MW chitosan fibers. The average Young's modulus (tensile elastic modulus) of the chitosan mats were determined from the slope of the linear elastic region of the stress-strain curve and averaged among the samples. The Young's modulus (Table 3) of the as-spun and cross-linked fibers was found to be 154.9±40.0 and 150.8±43.6 MPa, respectively. The initial steep slope of the curves corresponds to the nanofibers' intrinsically high cohesive forces due to the large number of fiber-to-fiber contacts; therefore, the nanofibrous mats have a high resistance to deformation. FIG. 20 displays a typical stress-strain plot of as-spun medium MW chitosan fibrous mats containing 2.5% carbon black (FIG. 20B) and (c) vapor-cross-linked medium MW chitosan fibrous mats containing 2.5% carbon black (FIG. 20C).

A pseudo-yield point is present in the as-spun fibers stress-strain plot as evident by the second portion of the increasing slope that increases at a reduced rate. Hence, a reduced increase in modulus is observed, which corresponds to fiber alignment along the tensile pull axis. As the once randomly aligned fibers are being aligned, there is an increase in the allowable stresses until the break strain and ultimate tensile strength are achieved; they average (Table 3) 0.12±0.03 and 4.07±0.80 MPa, respectively, for the as-spun medium MW chitosan fibers.

The graph of the vapor-cross-linked medium MW fibers does not display the same pseudo-yield point but features a distinct maximum where the break occurred during tensile pulling. This loss might be indicative that the individual fibers have become locked together and therefore cannot slip past each other as demonstrated by the as-spun fibrous mats. The vapor-cross-linked medium MW fibers have a lower average break strain (Table 3) of $0.10\pm(8.49\times10^{-5})$ and additionally a decreased ultimate tensile strength of $1.19\pm0.0041$ MPa in comparison with the as-spun fibers. No mechanical data have been reported on electrospun chitosan or chitosan/polymer nanofibers or nanofibrous mats. Mechanical data concerning electrospun chitosan fibrous mats with various amounts of carbon black are displayed (Table 4). Mechanical properties of chitosan fibers created by traditional techniques such as wet-spinning have been evaluated. Knaul et al. (Knaul, J. Z.; Hudson, S. M.; Creber, K. A. M. J. Polym. Sci., Part B: Polym. Phys. 1999, 37 (11), 1079-1094) mechanically tested wet-spun chitosan fibers with various concentrations of GA cross-linker They found that modulus, break, and tenacity decreased while brittleness increased after a particular amount of cross-linking agent was employed. Thus, they proposed that the dialdehyde degrades the molecular structure at high concentrations of GA or that stress concentrations might form within the fibers.

The previously described distinct difference in the elasticity of the as-spun versus vapor-cross-linked fibers can be supported by the SEM images (FIG. 8). These images were taken in close proximity to the failure point of the fiber mats so that changes in individual fiber morphology could be observed. FIG. 8 (top left) displays an image of as-spun fibers after mechanical testing that contains both aligned fibers and a multitude of cracks or locations where extensions occurred on the fibers prior to their ultimately breaking. The zoomed-in image, FIG. 8 (right), displays cracks that propagated perpendicular to the long axis of the fiber. This phenomenon shows the elastic nature of the as-spun fibers. The lower left image in FIG. 8 exhibits that the vapor-cross-linked fiber mats retained their randomly oriented fiber composition and experienced a multitude of broken fibers prior to their ultimate break. Vapor-cross-linked fibers did not demonstrate alignment or elongation prior to their failure; it can be concluded that they act less elastically than the as-spun chitosan nanofibers.

Table 3, below, provides mechanical property data of electrospun as-spun and vapor cross-linked medium molecular weight chitosan fibrous mats:

TABLE 3

|  | As-spun fibers | Cross-linked fibers |
|---|---|---|
| Young's modulus (MPa) | 154.9 ± 40.0 | 150.8 ± 43.6 |
| Break strength | 0.12 ± 0.03 | 0.10 ± (8.49 × 10$^{-5}$) |
| Ultimate tensile strength (MPa) | 4.07 ± 0.80 | 1.19 ± 0.0041 |

Table 4, below, provides mechanical property data of electrospun as-spun and vabor cross-linked medium molecular weight chitosan fibrous mats containing various amounts of carbon black filler material:

Fibrous mats were successfully electrospun from low, medium, and high molecular weight as well as practical-grade chitosan.

All chitosans were capable of being electrospun into fiber mats without exhibiting any branching. When electrospun under certain conditions, the low MW and practical-grade chitosan fibers displayed branching.

From the data collected on the average fiber diameter of as-spun and cross-linked chitosan fibers, it can be concluded that vapor-cross-linking increases the average fiber diameter, which is most likely due to the GA bonding to the chitosan and thus stretching the molecules. Cross-linking during production results, on average, in smaller diameter chitosan fibers compared to cross-linking post-production.

Cross-linking with GA made the chitosan fiber and chitosan-additive fiber mats insoluble in NaOH, acetic acid, and ultrapure water solutions for at least 72 h.

The decreasing slope prior to the ultimate failure of the as-spun fiber mats indicates that these fibers experienced a reduced increase of mechanical properties prior to their breaking point. This can be attested to the lessening influence of cohesive forces (from the fiber-fiber contacts) and replacement with fiber alignment and pulling. Additionally, the SEM images confirm that the as-spun fibers developed cracks perpendicular to the length of the fibers that allowed the fibers to elongate. Alternatively, the cross-linked fibers did not experience a slow degradation of properties but rather a quick break, as supported by the SEM images of sharply broken fibers. The cross-linker effectively locked the chitosan fibers together, thus prohibiting fiber slippage and causing the loss of the pseudo-yield point.

FIGS. 9-17 show SEM images of electrospun chitosan nanofiber mats containing hyaluronic acid, nile red, diatomaceous earth (DE), calcium carbonate, limestone, metakaolinite, carbon black, and glutaraldehyde (GA). These are examples of the fillers and additives that can be used with the chitosan mats and are not intended to be limiting.

What is claimed:

1. A fibrous mat comprising chitosan nanofibers having an average diameter of about 50 to about 120 nanometers, wherein said fibrous mat is substantially free of fibers of polyethylene oxide or fibers of poly(vinyl alchohol), and wherein said chitosan nanofibers are electrospun from chitosan.

2. The fibrous mat according to claim 1 further comprising a filler material.

3. The fibrous mat of claim 2, wherein the at least one filler material is clay, diatomaceous earth, calcium carbonate, metakaolinite, limestone, carbon black, or mixtures thereof.

4. The fibrous mat of claim 2 comprising about 0.1% to about 60% by weight of said filler material.

5. The fibrous mat of claim 1, wherein the chitosan is cross-linked after fiber production.

TABLE 4

| CB (%) | Ultimate Tensile Strength (MPa) | | Break Strain | | Young's Modulus (Mpa) | |
|---|---|---|---|---|---|---|
|  | As-spun | Cross-linked | As-spun | Cross-linked | As-spun | Cross-linked |
| 0.00 | 4.07 ± 0.8 | 1.19 ± 0.8 | 0.12 ± 0.03 | 0.10 ± 8 × 10−5 | 155 ± 40 | 151 ± 40 |
| 2.50 | 0.677 ± 0.0004 | 0.274 ± 0.08 | 0.00281 ± 0.0003 | 0.00233 ± 0.0006 | 0.128 ± 0.009 | 0.147 ± 0.03 |
| 6.25 | 0.579 ± 0.02 | 0.393 ± 0.03 | 0.00180 ± 0.0002 | 0.00210 ± 0.001 | 0.0640 ± 0.01 | 0.165 ± 0.06 |
| 60.0 | 0.403 ± 0.0006 | 0.411 ± 0.03 | 0.0016 ± 0.0006 | 0.0008 ± 0.0001 | 0.0669 ± 0.04 | 0.0615 ± 0.01 |

6. The fibrous mat of claim 5, wherein the chitosan is cross-linked using glutaraldehyde vapor.

7. The fibrous mat of claim 1, wherein the chitosan is cross-linked during fiber production.

8. The fibrous mat according to claim 1 further comprising at least one additive.

9. The fibrous mat of claim 8, wherein the at least one additive comprises a dye, polymer, particle, nanoparticle, organic molecule, or any combination thereof.

10. The fibrous mat of claim 9, wherein the dye is nile red or phthalocynanine green.

11. The fibrous mat of claim 9, wherein the polymer comprises hyaluronic acid, alginate, chitin, carboxymethylated chitosan, or any combination thereof.

12. The fibrous mat of claim 9, wherein the at least one additive comprises particles or nanoparticles comprising manganese, gold, silver, copper, platinum, palladium, or any combination thereof.

13. The fibrous mat of claim 9, wherein the organic molecule is a cross-linker, a protein, or an enzyme.

14. The fibrous mat of claim 13, wherein the organic molecule comprises a cross-linker, and the cross-linker comprises glutaraldehyde.

15. The fibrous mat of claim 8 wherein the nanofibers consist essentially of chitosan.

16. The fibrous mat of claim 8 further comprising at least one filler material, wherein the filler material is clay, diatomaceous earth, calcium carbonate, metakaolinite, limestone, carbon black, or mixtures thereof.

17. The fibrous mat according to claim 16 comprising about 0.1% to about 60% by weight of said filler material.

18. A filter comprising a fibrous mat according to claim 8.

19. A scaffold comprising a fibrous mat according to claim 8.

20. The fibrous mat according to claim 1 wherein said chitosan nanofibers are electrospun from chitosan in the presence of a tri-halo carboxylic acid solvent.

21. A filter comprising a fibrous mat according to claim 1.

22. A scaffold comprising a fibrous mat according to claim 1.

* * * * *